United States Patent

Haber et al.

[11] Patent Number: 5,217,480
[45] Date of Patent: Jun. 8, 1993

[54] CAPILLARY BLOOD DRAWING DEVICE

[75] Inventors: Terry M. Haber, El Toro; Clark B. Foster, Laguna Niguel; William H. Smedley, Lake Elsinore, all of Calif.

[73] Assignee: Habley Medical Technology Corporation, Laguna Hills, Calif.

[21] Appl. No.: 895,893

[22] Filed: Jun. 9, 1992

[51] Int. Cl.⁵ ............................................. A61B 17/32
[52] U.S. Cl. .................................................... 606/182
[58] Field of Search ............... 128/763, 765, 767, 770, 128/760; 606/181–183

[56] References Cited

U.S. PATENT DOCUMENTS

| | | |
|---|---|---|
| 3,659,608 | 5/1972 | Perry . |
| 3,662,928 | 5/1972 | Pogorski et al. ............... 128/763 |
| 3,785,367 | 1/1974 | Fortin et al. . |
| 4,172,448 | 10/1979 | Brush ............................. 128/767 |
| 4,187,860 | 2/1980 | Villari ............................. 128/767 |
| 4,245,655 | 1/1981 | Patel .............................. 128/767 |
| 4,298,011 | 11/1981 | Mangurten et al. . |
| 4,360,016 | 11/1982 | Sarrine . |
| 4,385,637 | 5/1983 | Akhavi . |
| 4,414,975 | 11/1983 | Ryder et al. . |
| 4,539,988 | 9/1985 | Shirley et al. . |
| 4,643,200 | 2/1987 | Jennings, Jr. . |
| 4,715,374 | 12/1987 | Maggio . |
| 4,883,068 | 11/1989 | Dechow . |
| 4,892,097 | 1/1990 | Ranalletta . |
| 5,054,499 | 10/1991 | Swierczek ...................... 606/182 |

FOREIGN PATENT DOCUMENTS 2017497 10/1979 United Kingdom ............... 128/767
8504089 9/1985 World Int. Prop. O. .

Primary Examiner—Max Hindenburg
Attorney, Agent, or Firm—Hawes & Fischer

[57] ABSTRACT

A compact, efficient and disposable capillary blood drawing device by which a patient's tissue can be punctured and a blood sample collected by the same reliable device. The blood drawing device includes the integral connection of a solid core needle and a spring in which potential energy is initially stored. A release of the potential energy from the spring correspondingly causes the needle to be driven into contact with the patient's tissue to make a puncture therein. When the spring assumes an at rest position, the needle will be safely withdrawn in and shielded by the blood drawing device to avoid an accidental needle stick and the possible spread of disease. The blood drawing device also includes a flexible bladder in which blood from the puncture can be collected, under suction, and selectively expulsed, under compression, for medical examination and diagnostic purposes.

20 Claims, 3 Drawing Sheets

CAPILLARY BLOOD DRAWING DEVICE

FIELD OF THE INVENTION

This invention relates to a disposable capillary blood drawing device by which a patient's tissue may be punctured and a blood sample collected and dispensed by means of the same compact, relatively low cost device.

BACKGROUND ART

Prior art lancing devices are known by which to puncture a patient's skin and to collect a sample of the patient's blood for medical evaluation and diagnosis. However, separate devices are commonly used to first puncture the patient's skin and then collect the blood sample. An additional device may also be needed to dispense an adequate volume of blood from the collector so as to permit a suitable medical examination of the sample. Obviously, the need for separate lancing, collecting and dispensing devices increases medical costs and reduces efficiency. Moreover, the disposal volume is also significantly increased when separate lancing and collecting devices must be safely discarded. Likewise, the preparation of such prior art devices for use (e.g. arming the lancing device with a removable tissue puncturing needle) may be complicated and require special skill and/or care.

In some cases, access is available to the tissue puncturing needle before and/or after the patient's tissue has been punctured. Therefore, both sheathing and re-sheathing steps may be required to adequately shield the tip of the needle. In other cases, there is no easy way to reliably isolate the blood sample in the blood collection device from the outside environment. Consequently, an accidental needle stick from the lancing device or the premature expulsion of blood from the collecting device could lead to the spread of a contageous and possible life threatening disease. That is to say, the lack of any protective means or the misuse of said protective means with conventional lancing and blood collecting devices will subject health care workers to increased risk of disease during the handling, use and disposal of such conventional devices.

SUMMARY OF THE INVENTION

In general terms, a compact, low cost and disposable capillary blood drawing device is disclosed having means by which a patient's tissue may be punctured and a blood sample collected without requiring the separate lancing and blood collecting devices of the prior art. The blood drawing device includes a pair of support arms that are hingedly connected together and rotatable relative to one another. Located between the arms is a hollow, inflatable blood collecting bladder having a spring-like resiliency to normally bias the arms of the blood collector in a spaced relationship. A safety flap is removably connected between the arms to prevent a rotation of the arms towards one another and a premature compression of the bladder.

One of the support arms of the blood drawing device is provided with a hollow interior. Located within the hollow interior are a tissue puncturing needle and a spring. The spring and needle are integrally connected to one another such that the needle is formed at one end of the spring. One end of the spring is fixed, and the other end of the spring is stressed (i.e. stretched) so as to be engaged and retained by a retaining ledge, whereby the spring stores potential energy. The support arm of the blood drawing device without the integral spring and needle carries a needle release projection which is movable into contact with the spring so as to release the spring from engagement with the retaining ledge when the support arms of the blood drawing device are rotated towards one another.

In operation, with the spring initially retained by the retaining ledge, the arms of the blood drawing device are rotated towards one another, whereby to move the needle release projection at one support arm into contact with the spring at the other support arm. Accordingly, the spring is moved out of engagement with the spring retaining ledge so that stored energy is released therefrom for driving the needle out of its support arm to penetrate the patient's tissue. However, when the spring assumes an unstressed, at rest position, the needle is correspondingly withdrawn into and safely shielded at the interior of the support arm. The aforementioned rotation of the arms towards one another also compresses the bladder therebetween. As the arms are subsequently rotated away from one another, the bladder expands, whereby to be infused, by means of suction, with the patient's blood. Another rotation of the arms towards one another compresses the bladder and expulses the blood sample therefrom for medical examination and diagnosis.

DESCRIPTION OF THE PREFERRED EMBODIMENT

Figure 1:
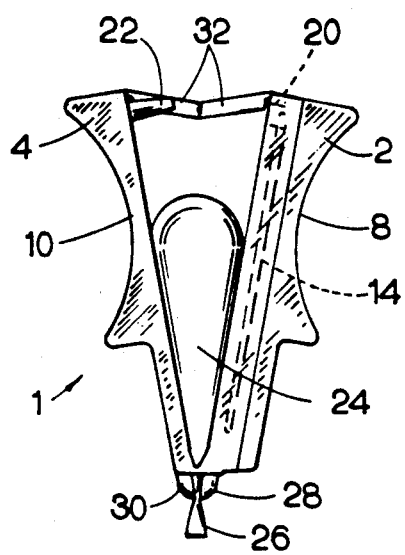
FIG. 1 is a side view of the capillary blood drawing device which forms the present invention.

The compact, disposable capillary blood drawing device which forms the present invention is best described while referring to drawings, where FIGS. 1-4 show the blood drawing device 1 in the as-packaged configuration. The blood drawing device 1 is preferably formed from a lightweight, easily molded material, such as polyethylene, polypropylene, and the like. Blood drawing device 1 includes a pair of support arms 2 and 4 that are pivotally connected together at first ends thereof by means of an integral or living hinge 6. The opposite ends of support arms 2 and 4 extend outwardly from hinge 6 so as to form an angle therebetween of approximately 15 to 30 degrees. Molded into the front faces of each support arm 2 and 4 is an arcuate finger rest 8 and 10 at which the thumb and forefinger of a medical worker are received (best shown in FIGS. 5-10) so that operation of the blood drawing device 1 may be reliably controlled.

Figure 2:
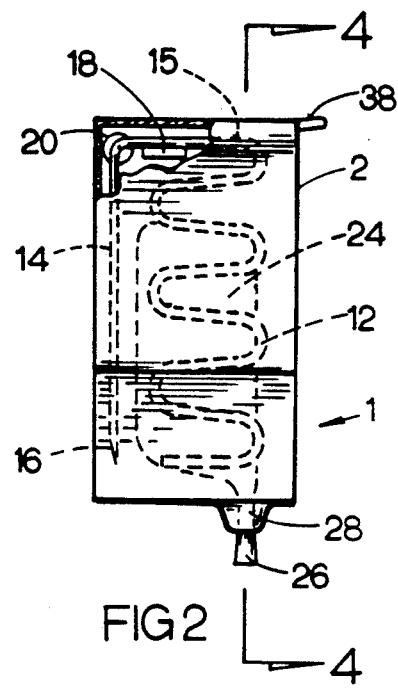
FIG. 2 is a front view of the capillary blood drawing device of FIG. 1.
Figure 3:
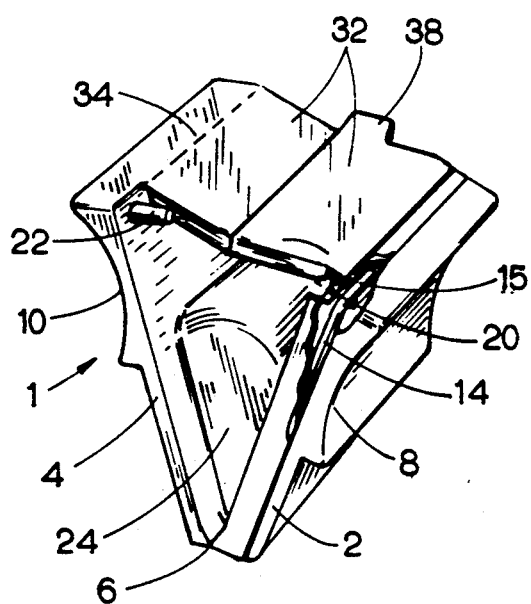
FIG. 3 is a perspective view of the capillary blood drawing device.
Figure 4:
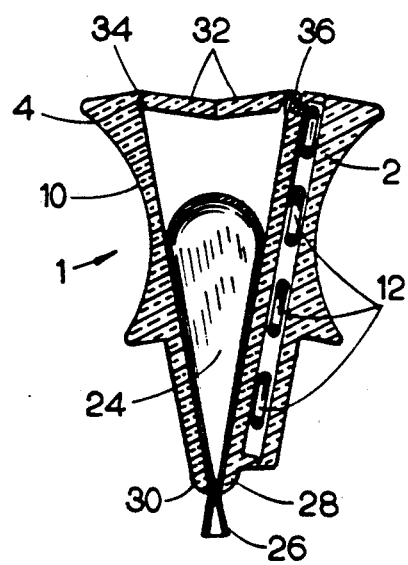
FIG. 4 is a cross-section taken along lines 4—4 of FIG. 2.

One of the support arms (e.g. 2) of capillary blood drawing device 1 is of hollow construction. Located within the interior of hollow arm 2 is a metallic, solid core spring 12. Although the spring 12 can be of any configuration, it is preferable that spring 12 extend lengthwise through arm 2 and have a rippled configuration so that potential energy can be stored by spring 12 in the as-packaged configuration and efficiently transferred to a puncture producing needle, in a manner that will be described in greater detail hereinafter. To this end, the puncture producing needle 14 is integrally connected t spring 12, such that needle 14 is formed at one end of spring 12. The needle 14 is of solid cross section and terminates at a sharp sterile tip 16 that is capable of penetrating a patient's tissue for the purpose of drawing one or more drops of blood. As is best shown in FIG. 2, needle 14 is a straight piece of metal that extends lengthwise through the interior of support arm 2 in the same plane as spring 12. In the as-packaged configuration of FIGS. 1-4, the tip 16 of needle 14 is safely retracted within the interior of support arm 2 so as to avoid an accidental needle stick and the loss of sterility. One end of spring 12 is fixed, while the opposite end 15 to which needle 14 is connected is free to move.

A spring retaining ledge 18 projects into the hollow interior of support arm 2 from the rear face thereof. In the as-packaged configuration, and as best shown in FIG. 2, the free end 15 of spring 12 is engaged by ledge 18. That is to say, such free end 15 is initially received and retained behind ledge 18 so as to stress or expand spring 12 from its normally relaxed condition and thereby cause potential energy to be stored within said spring. Moreover, needle 14 is held at a ready position with the tip 16 thereof shielded at the interior of support arm 2.

An opening 20 is formed through the rear face of support arm 2 opposite the location at which the free end 15 of spring 12 is received and retained by ledge 18 in the as-packaged condition. A spring release tab 22 project outwardly from support arm 4 in spaced, opposing alignment with the opening 20 through support arm 2. As will soon be described, the arms 2 and 4 of blood drawing device 1 may be rotated towards one another around hinge 6 to cause the needle release tab 22 of arm 4 to be received within the opening 20 of arm 2 and thereby disengage the free end 15 of spring 12 from spring retaining ledge 18 so as to permit spring 12 to return to its normally relaxed state. Accordingly, potential energy stored within spring 12 will be released to drive the tip 16 of needle 14 outwardly of support arm 2 and into the tissue of a patient.

Blood drawing device 1 includes a hollow, compressible blood collecting bladder 24 which is located between the support arms 2 and 4. Bladder 24 has a spring-like resiliency to normally bias arms 2 and 4 in the spaced V-shaped alignment, as shown. Bladder 24 may either be detachable from blood drawing device 1 or integrally connected thereto, such as at living hinge 6. A hollow bladder tube 26 communicates at one end thereof with the interior of bladder 24. The opposite end of bladder tube 26 extends outwardly from blood drawing device 1 through a hole in the hinge 6 and between a pair of opposing jaws 28 and 30 which are coextensively formed with support arms 2 and 4, respectively. In the as-packaged configuration of FIGS. 1-4, with the support arms 2 and 4 of blood drawing device 1 spaced from one another, the jaws 28 and 30 of said arms ar correspondingly positioned to pinch off the hollow bladder tube 26 and thereby block communication with the interior of bladder 24 so as to avoid possible contamination of said bladder by dirt moisture and the like.

To preserve the spaced alignment of the arms 2 and 4 of blood drawing device 1 in the as-packaged configuration and thereby prevent an accidental and premature firing of the needle 14 and ejection of needle tip 16, a safety lock is removably extended between the arms 2 and 4. By way of example, the safety lock is a segmented flap 32, one end of which is pivotally connected to one of the support arms 4 by means of an integral hinge 34. The opposite end of safety flap 32 has a lip that is snap-fit within a receptacle 36 formed in the other support arm 2. Accordingly, the safety flap 32 extends between the support arms 2 and 4 of blood drawing device 1 to assume a locked position at which to prevent said arms from being rotated towards one another around hinge 6 whereby to block a release of spring 16 and the inadvertent firing of needle 14. As will soon be described, the segmented safety flap 32 may be detached from receptacle 36 and folded or collapsed around a medial seam to an unlocked position when it is desirable to fire the needle 14 and thereby draw a blood sample from the patient. To facilitate the foregoing, an access tab 38 extends outwardly from one of the segments of safety flap 32. By lifting tab 38, the lip of safety flap 32 may be disengaged from receptacle 36 such that the segments of flap 32 may be folded against one another to permit the support arms 2 and 4 of blood drawing device 1 to be rotated towards one another around hinge 6.

Figure 5:
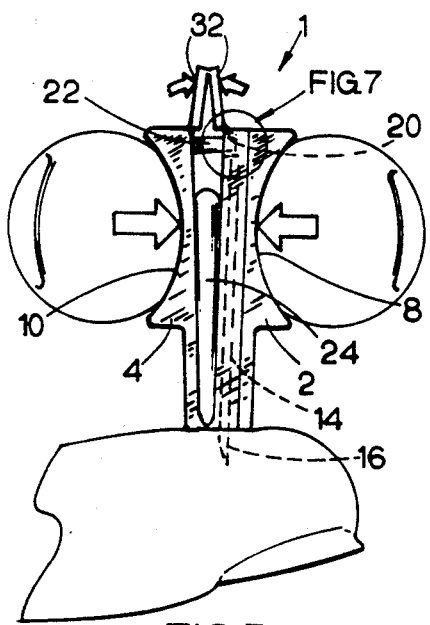
FIGS. 5 and 6 illustrate the operation of the capillary blood drawing device for puncturing a patient's tissue by means of a needle.
Figure 6:
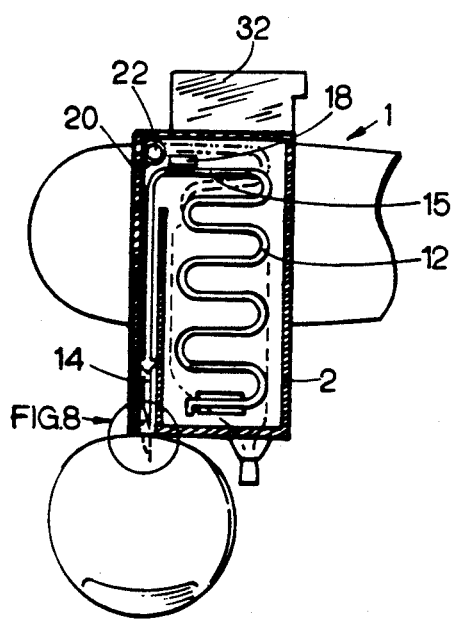

The operation of capillary blood drawing device 1 is now described while referring to FIGS. 5-10 of the drawings. In FIG. 5 and 6, the blood drawing device 1 is shown with the safety flap 32 folded to an unlocked position to permit support arms 2 and 4 to be rotated towards one another. To this end, the health care worker locates his thumb and forefinger at respective finger rests 8 and 10 of arms 2 and 4 by which to apply equal and opposite axial forces thereto for rotating arms 2 and 4 together (in the direction of the reference arrows) with blood collecting bladder 24 being compressed therebetween. As the support arm 4 is moved towards the support arm 2, the spring release projection 22 of arm 4 is correspondingly rotated through the opening 20 of arm 4. Accordingly, projection 22 is moved into contact with the free end 15 of spring 12. As previously indicated, the free end 15 is initially located behind the spring retaining ledge 18 in the as-packaged configuration of blood drawing device 1 (shown in phantom in FIG. 6), whereby needle 14 is held at a ready position. The continued movement of spring release projection 22 through opening 20 eventually causes the free end 15 of spring 12 to be displaced laterally and moved out of engagement with spring retaining ledge 18 so as to release the stored energy from spring 12 and thereby drive tip 16 of needle 14 outwardly from the support arm 2 in which needle 14 is housed.

Figure 7:
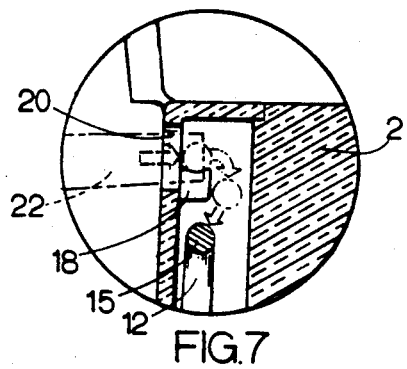
FIGS. 7 and 8 are details taken from FIGS. 5 and 6, respectively.
Figure 8:
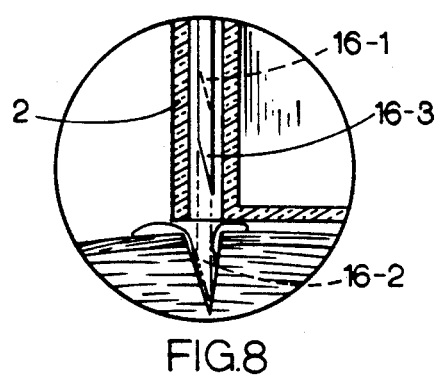

More particularly, and referring briefly to FIG. 7, the spring release projection 22 (of support arm 4) is shown moving through the opening 20 of support arm 2 in order to contact the free end 15 of spring 12 so as to move spring 12 laterally and out of engagement with spring retaining ledge 18. Thus, the potential energy stored when the free end 15 of spring 12 is retained by ledge 18 is released, and the integral needle is automatically driven by spring 12 to an activated position so as to penetrate the tissue of the patient Referring concurrently to FIGS. 5, 6 and 8 of the drawings, the tip 16 of needle 14 is shown before, during and after penetrating the tissue of the patient. In FIG. 8, the tip of needle 14 is depicted in each of three positions corresponding, respectively, to a first position where spring 12 is stretched so as to store potential energy and needle tip 16-1 is located at a ready position within the hollow interior of support arm 2, a second position where the potential energy of the spring is released and the needle tip 16-2 is driven to an activated position outwardly from support arm 2 to penetrate the patient's tissue and draw a blood sample therefrom, and a third position where the spring returns to its unstressed (i.e. relaxed) condition at which the needle tip 16-3 is at rest and received back into the support arm 2 to avoid an accidental needle stick and the possible spread of disease. Thus, it can be observed that the memory of spring 12 when returning to its relaxed position after the patient's tissue has been punctured results in the tip 16-3 of integral needle 14 being returned to and safely shielded within the hollow interior of arm 2.

Figure 11:
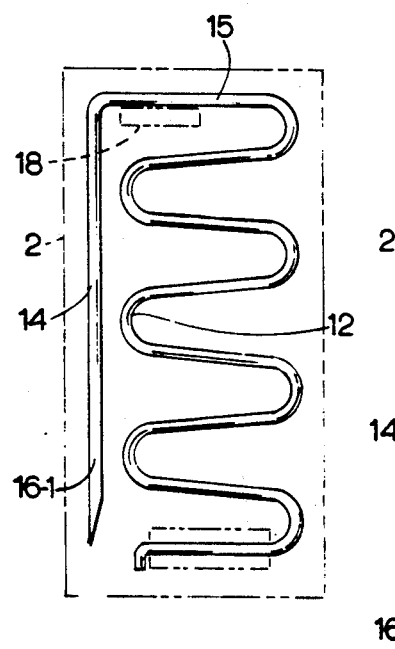
FIGS. 11-13 show the location of the tissue puncturing needle in ready, activated and at-rest positions, respectively.
Figure 12:
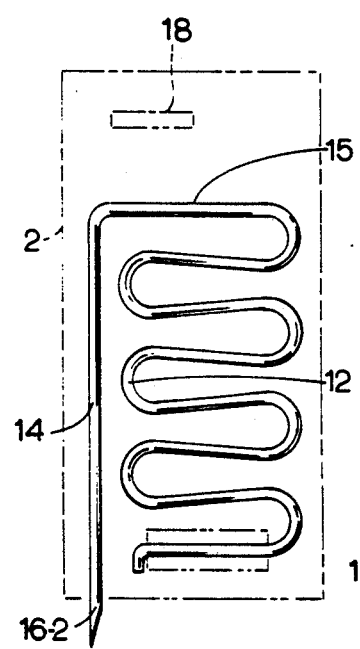
Figure 13:
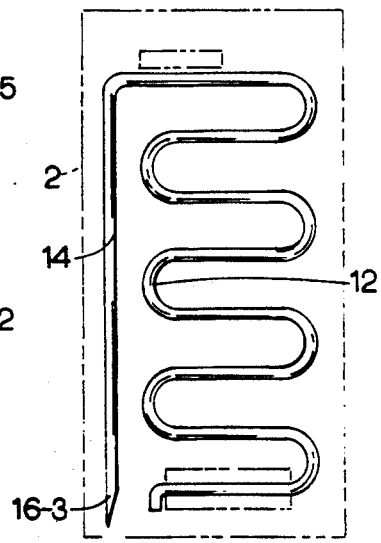

The foregoing may be better understood while referring to FIGS. 11-13 of the drawings in which the tip of needle 14 is shown in each of the aforementioned ready, activated, and at rest positions of FIG. 8. In FIG. 11, the free end 15 of spring 12 is initially located behind the needle retaining ledge 18, whereby the spring 12 is stressed and potential energy is stored therein. The tip 16-1 of needle 14 is retained, in the ready position, within the hollow interior of support arm 2.

In FIG. 12, the free end 15 of spring 12 is moved away from ledge 15 (i.e. by means of moving the spring release projection 22 of FIG. 7 into contact therewith), whereby the stored potential energy within spring 14 is released to cause the spring to become slightly compressed. The tip 16-2 of needle 14 is driven to the activated position by integral spring 12 and moved outwardly from the interior of support arm 2 so as to penetrate the tissue of the patient.

In FIG. 13, the spring 12 returns to its normal, unstressed or relaxed configuration, whereby the tip 16-3 of integral needle 14 is automatically retracted to the at-rest position to be safely shielded by and rendered inaccessible within the hollow interior of arm 2.

Figure 9:
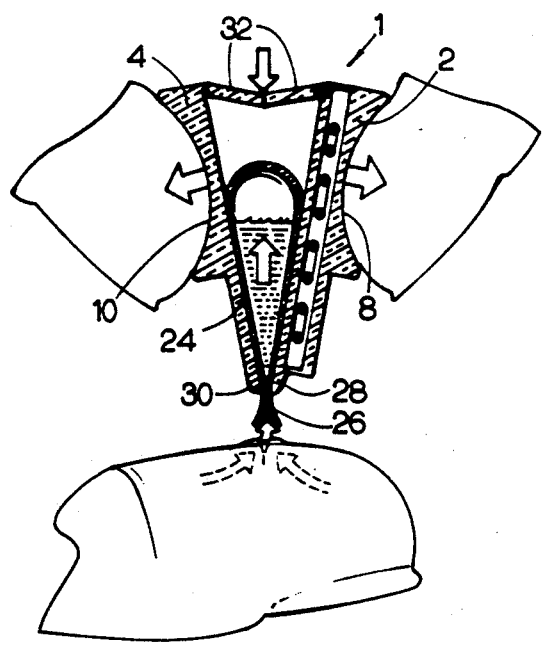
FIG. 9 illustrates the operation of the capillary blood drawing device and a blood collecting bladder thereof being infused with a sample of the patient's blood.

FIG. 9 of the drawings shows the bladder 24 of capillary blood drawing device 1 being infused with blood from the puncture produced by needle 14. As previously indicated, bladder 24 is compressed when the support arms 2 and 4 of blood drawing device 1 are rotated towards one another. As was also previously disclosed, the blood drawing device 1 is normally biased, in the as-packaged configuration, by bladder 24 so that support arms 2 and 4 will automatically move away from one another. Therefore, by releasing the forces applied at the finger rests 8 and 10 of support arms 2 and 4, the bladder acts as an expanding spring to cause the arms 2 and 4 to rotate (in the direction of the reference arrows). The expansion of bladder 24 also automatically draws the patient's blood therewithin, by means of suction, via bladder tube 26. With bladder 24 fully expanded and arms 2 and 4 rotated away from one another, the integral jaws 28 and 30 of support arms 2 and 4 are correspondingly rotated towards one another to pinch off the bladder tube 26. Accordingly, the bladder 24 and the blood sample stored therewithin are isolated from the surrounding environment at the constricted portion of bladder tube 26, whereby to prevent a contamination of the blood sample. What is more, the segmented safety flap 32 may be unfolded and extended between support arms 2 and 4 to prevent both an inadvertent compression of bladder 24 and a premature expulsion of the blood stored therewithin.

Figure 10:
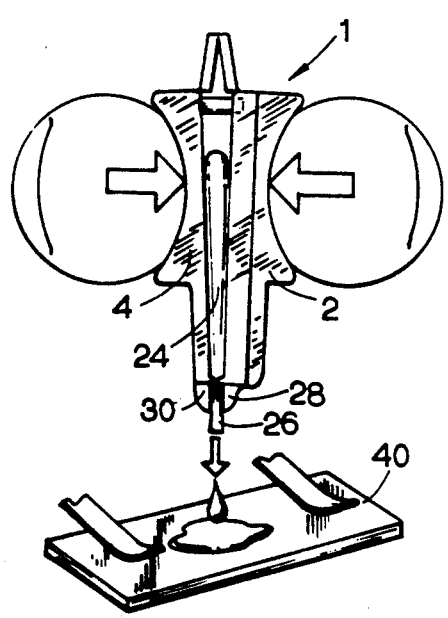
FIG. 10 illustrates the operation of the capillary blood drawing device for expulsing the sample of blood from the bladder for medical examination and diagnostic purposes.

In FIG. 10 of the drawings, the capillary blood drawing device 1 in which a blood sample is stored is transported to a medical testing facility. At this time, one or more droplets of the blood sample can be expulsed from the bladder 24 for receipt upon a medical slide 40, or the like, for evaluation and examination. The foregoing is accomplished by rotating the support arms 2 and 4 of blood drawing device 1 towards one another (in the direction of the reference arrows) to compress the bladder 24 therebetween. Rotating the arms 2 and 4 towards one another also rotates the jaws 28 and 30 of blood drawing device 1 away from one another to remove the constriction of the bladder tube 26. The compressive forces applied to bladder 24 correspondingly causes blood to be expulsed therefrom, under pressure, via bladder tube 26.

Once a blood sample has been deposited on slide 40, the capillary blood drawing device 1 of the present invention may be discarded. However, any remaining blood from the sample stored in bladder 24 may be safely isolated from the environment at the pinched off constriction of bladder tube 26 produced by the jaws 28 and 30 when support arms 2 and 4 are permitted to rotate away from one another. Moreover, the needle which punctures the patient's skin is safely shielded by and rendered inaccessible within the hollow interior of the support arm 2. Therefore, the blood drawing device 1 may be handled and discarded while substantially reducing the chance of an accidental needle stick, whereby the spread of a contagious and possible life threatening disease can be avoided. What is even more, it should be apparent that the puncture producing needle and the bladder in which a blood sample is collected and from which the sample is dispensed are part of the same compact device. Accordingly, and by virtue of the present invention, the patient's tissue may be pierced and a blood sample collected and dispensed with increased efficiency, lower cost and enhanced safety.

It will be apparent that while a preferred embodiment of the invention has been shown and described, various modifications and changes may be made without departing from the true spirit and scope of the invention. Having thus set forth a preferred embodiment of the preferred invention, what is claimed is:

We claim:

1. A capillary blood drawing device comprising:
    means by which to puncture the tissue of a patient so as to draw blood therefrom;
    flexible blood collecting means adapted to be in either a compressed or expanded condition, said blood collecting means being in a compressed condition while the patient's tissue is being punctured, said blood collecting means being in an expanded condition after the tissue is punctured so as to be infused with a blood sample by means of suction, and said blood collecting means being in a compressed condition after being infused with said blood sample so as to expulse the sample therefrom for medical examination and diagnostic purposes; and means engaging said blood collecting means and movable therewith for successively compressing and expanding said blood collecting means to cause said blood collecting means to be infused with or expulse the patient's blood sample.

2. The capillary blood drawing device recited in claim 1, wherein said tissue puncturing means includes a spring and a needle interconnected with said spring, said blood drawing device further comprising means by which to retain said spring at a first position so that potential energy is stored within said spring, and means by which to release said spring from said spring retaining means to correspondingly release energy stored by said spring for causing a movement of said needle to puncture the tissue of the patient.

3. The capillary blood drawing device recited in claim 2, further comprising first and second support means which are movable reciprocally towards and away from one another, said spring and said spring retaining means located at a first of said support means and said spring release means located at the second support means, such that said spring release means moves into contact with and releases said spring from said spring retaining means when said first and second support means are moved towards one another.

4. The capillary blood drawing device recited in claim 3, further comprising blocking means releasably connected between said first and second support means to block the movement of said first and second support means towards one another and thereby prevent said spring release means from moving into contact with and releasing said spring.

5. The capillary blood drawing device recited in claim 3, wherein said first and second support means are arms that are pivotally connected together at respective first ends thereof, the opposite ends of said arms being normally spaced from and rotatable towards one another for moving said spring release means into contact with said spring to release said spring from said spring retaining means.

6. The capillary blood drawing device cited in claim 3, wherein said first support means includes a hollow compartment at the interior thereof, said spring and said spring retaining means located within said hollow compartment.

7. The capillary blood drawing device recited in claim 6, wherein said first support means includes an opening communicating with said hollow compartment thereof, said spring release means moving into contact with said spring within said compartment by way of said opening.

8. The capillary blood drawing device recited in claim 3, wherein said blood collecting means is a compressible bladder located between said first and second support means, said bladder being infused with or expulsing the patient's blood sample depending upon whether said support means are moved towards or away from one another so as to either compress or release said bladder.

9. The capillary blood drawing device recited in claim 8, further comprising releasable closure means by which to close said bladder and thereby prevent the contamination of or loss of blood from said bladder.

10. A capillary blood drawing device to puncture a patient's tissue and collect a sample of the blood drawn from the puncture, said blood collector comprising:

needle means movable towards the patient's tissue to make the puncture therein;

spring means to control the movement of said needle means;

flexible bladder means in which to collect the patient's blood by means of suction; and means by which to successively expand and compress said bladder to cause said bladder to be infused with or expulse the patient's blood.

11. The capillary blood drawing device recited in claim 10, wherein said needle means and said spring means are connected together, such that said needle means is located at one end of said spring means.

12. The capillary blood drawing device recited in claim 10, further comprising first and second support arms pivotally interconnected with and successively rotated away from and then towards one another, said bladder means located between said support arms so as to be either expanded or compressed and thereby infused with or emptied of the patient's blood depending upon whether said support arms are rotated away from or towards one another.

13. The capillary blood drawing device recited in claim 12, wherein said needle means and said spring means are carried on a first of said support arms.

14. The capillary blood drawing device recited in claim 13, wherein said first support arm is of hollow construction, said needle means and said spring means located at the hollow interior of said support arm.

15. The capillary blood drawing device recited in claim 13, further comprising needle retaining means carried on said first support arm to retain said spring means at a first position so that potential energy is stored by said spring means, and spring release means carried on the second of said support arms and movable into contact with said spring means at said first support arm when said first and second arms are rotated towards one another so as to release said spring means from said needle retaining means to correspondingly release energy stored by and spring means for causing a movement of said needle means to puncture the patient's tissue.

16. A capillary blood drawing device comprising:

needle means by which to puncture the tissue of a patient so as to draw blood therefrom, said needle means being movable between shielded and unshielded locations;

locking means by which to retain said needle means at said shielded location so as to avoid contact with the patient's tissue;

inflatable blood collecting means adapted to be in either a compressed or expanded condition, said blood collecting means being in the compressed condition while the patient's tissue is being punctured, and said blood collecting means being in the expanded condition after the tissue is punctured so as to be infused with a blood sample by means of suction;

means for compressing and expanding said blood collecting means to cause said blood collecting means to be evacuated or infused with the patient's blood; and needle releasing means movable into engagement with said locking means when said blood collecting means is compressed so as to release said needle means from said shielded location for movement to said unshielded location at which to puncture the patient's tissue.

17. The capillary blood drawing device recited in claim 16, wherein said needle means is interconnected at one end thereof with a spring, said spring storing potential energy when said locking means retains said needle means at said shielded location, and said spring releasing the stored energy to move said needle means to said unshielded location when said needle releasing means moves into engagement with said locking means to release said needle means from said shielded location.

18. The capillary blood drawing device recited in claim 16, wherein said means for compressing ;and expanding said blood collecting means includes a pair of support arms pivotally connected together at respective first ends thereof, the opposite ends of said support arms being spaced from and rotatable towards one another, said blood collecting means positioned between the respective opposite ends of said support arms.

19. The capillary blood drawing device recited in claim 18, wherein a first of said pair of support arms includes a hollow compartment in which said needle means is received when said needle means is at said shielded location, said locking means retaining said needle means within said hollow compartment of said first support arm.

20. The capillary blood drawing device recited in claim 19, wherein the second of said pair of support arms includes said needle releasing means, said needle releasing means moving with said second support arm towards said first support arm and into engagement with said locking means to release said needle means from the shielded location within the hollow compartment of said first support arm for movement outwardly of said hollow compartment and to said unshielded location at which to penetrate the patient's tissue.

* * * * *